United States Patent [19]

Kurek

[11] 4,362,893
[45] Dec. 7, 1982

[54] PREPARATION OF C-NITROSODIARYLAMINES FROM DIARYLAMINES

[75] Inventor: Paul R. Kurek, Schaumburg, Ill.

[73] Assignee: UOP Inc., Des Plaines, Ill.

[21] Appl. No.: 270,037

[22] Filed: Jun. 3, 1981

Related U.S. Application Data

[63] Continuation-in-part of Ser. No. 112,761, Jan. 17, 1980, abandoned.

[51] Int. Cl.$^3$ .................. C07C 85/145; C07C 85/18; C07C 85/20
[52] U.S. Cl. ................................. 564/410; 564/431; 564/433; 564/441
[58] Field of Search ................ 564/410, 431, 433, 441

[56] References Cited

U.S. PATENT DOCUMENTS

| 2,046,356 | 7/1936 | Wyler et al. | 260/69 |
| 2,419,718 | 4/1947 | Kehe | 564/410 |
| 2,495,774 | 1/1950 | Roberts | 260/577 |
| 2,560,892 | 7/1951 | Roberts | 260/576 |
| 2,560,893 | 7/1951 | Roberts | 260/576 |
| 2,560,894 | 7/1951 | Roberts | 260/576 |
| 2,782,235 | 2/1957 | Lantz et al. | 260/576 |
| 3,429,924 | 2/1969 | Ellerbrook et al. | 564/410 |
| 3,728,392 | 4/1973 | Levy et al. | 564/410 |
| 3,748,362 | 7/1973 | Kinstler | 564/410 |
| 4,034,042 | 7/1977 | Wedemeyer et al. | 564/410 |
| 4,102,926 | 7/1978 | Usvyatsov et al. | 564/410 |

FOREIGN PATENT DOCUMENTS

| 2211341 | 9/1973 | Fed. Rep. of Germany | 564/410 |
| 411235 | 8/1963 | Japan | 564/112 |

OTHER PUBLICATIONS

Dost et al., "Chemical Abstracts", vol. 52, Abstract No. 4686g, (1958).

Primary Examiner—John Doll
Attorney, Agent, or Firm—James R. Hoatson, Jr.; Eugene I. Snyder; William H. Page, II

[57] ABSTRACT

C-Nitrosodiarylamines may be prepared in a single stage from diarylamines by adding alcoholic solutions of a hydrogen halide below the surface of a stirred mixture of the diphenylamine in an organic liquid containing water. The amount of water contained is critical, and amounts from about 1 to about 3 g per mole of diarylamine are preferred.

11 Claims, No Drawings

PREPARATION OF C-NITROSODIARYLAMINES FROM DIARYLAMINES

CROSS-REFERENCE TO RELATED APPLICATIONS

This application is a continuation-in-part of my now abandoned application Ser. No. 112,761, filed Jan. 17, 1980, all of which is hereby incorporated by reference.

BACKGROUND OF THE INVENTION

C-nitrosodiarylamines, by which is meant diarylamines where one of the aryl groups bears a nitroso group, and which can be represented by the formula ArNHAr—NO, are important intermediates in the production of articles of commerce. For example, p-nitrosodiphenylamine (PNODPA), which currently may be the most useful representative of the class of C-nitrosodiarylamines, is generally the precursor of p-aminodiphenylamine, whose derivatives are widely used as antioxidants and antiozonants.

Generally, C-nitrosodiarylamines are prepared by acid catalyzed rearrangement of the isomeric N-nitrosodiarylamines, represented by the formula $Ar_2N$—NO. As the precursor of PNODPA, N-nitrosodiphenylamine (NNODPA) may be viewed as the archtypical representative of the class of N-nitrosodiphenylamines.

The difficulties inherent in the preparation of PNODPA by acid catalyzed rearrangement of NNODPA are diverse. Because both PNODPA and NNODPA are carcinogens, there is obvious risk attending handling. If too high an acid concentration is used in the rearrangement of NNODPA, denitrosation occurs to afford tars and other color bodies difficult to remove, even from subsequent products. It is also known that the presence of water in amounts greater than about 12% adversely affects rearrangement in the presence of acids. Additionally, both PNODPA and NNODPA are thermally labile. Thus, temperatures in excess of about 60° C. commonly cause sufficient decomposition to afford undesirable color bodies and other unwanted materials.

The N-nitrosodiarylamines are usually prepared by nitrosation of diarylamines, represented by the formula $Ar_2NH$. Thus, the overall chemistry involved in preparing C-nitrosodiarylamines is described by reactions (1) and (2).

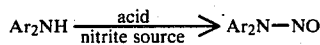

(1)

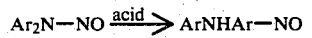

(2)

Because both reactions are usually performed in acidic media, in which both C- and N-nitrosodiarylamines form salts of the respective acid, it is to be explicitly understood that reference to C-nitrosodiarylamine or N-nitrosodiarylamine includes both the free base and a corresponding salt, unless noted otherwise.

Typically, the prior art methods of preparing C-nitrosodiarylamines utilize two discrete stages or sequences of operations. One stage corresponds to reaction (1), further characterized in that discrete operations are performed after formation of, but as a necessary prerequisite to rearrangement of, the N-nitrosodiarylamine. For example, the N-nitrosodiarylamine frequently is isolated prior to its rearrangement. As another example, the solution containing the N-nitrosodiarylamine may be treated so as to remove water, as by azeotropic distillation. Whatever the operation or treatment, the N-nitrosodiarylamine is thereafter rearranged to the C-nitrosodiarylamine in a second discrete stage whose operations correspond to reaction (2).

In contrast to the aforementioned staged method of preparing C-nitrosodiarylamines from diarylamines, the present invention relates to a process whereby the diarylamine is converted to product in but a single stage, as represented by reaction (3).

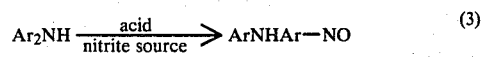

(3)

For the purposes of the present application, a single stage process is defined as one where two discrete chemical changes (corresponding to reaction (3)) are achieved by the continued addition of a reagent to a reaction mixture.

Single stage methods of preparing C-nitrosodiarylamines have been propounded. U.S. Pat. No. 2,046,356 describes a process of reacting a mixture comprising a solution of a diarylamine in an anhydrous alcohol containing suspended alkali metal nitrite with an anhydrous alcoholic solution of hydrogen chloride. Although the thrust of U.S. Pat. No. 2,782,235 is the rearrangement step, reaction (2) above, catalyzed by an aqueous solution of a hydrohalic acid, provided certain alcohols are present in the reaction medium, the patentees disclose also a single stage process whereby an aqueous solution of the hydrohalic acid acts on an alcoholic solution of a diarylamine containing suspended alkali metal nitrite. The patentee's claim that the amount of water present is not critical is contrary to the observations of the instant applicant.

In a series of related patents, Roberts describes a single stage process for the conversion of diarylamines to C-nitrosodiarylamines in alcoholic media containing an alkali metal nitrite by utilizing a chlorine containing compound to react with the water present to generate hydrogen chloride and maintain the reaction mixture in a substantially anhydrous condition. The chlorine containing compound is phosgene and other acid chlorides in U.S. Pat. No. 2,495,774; phosphorous trichloride and oxychloride in U.S. Pat. No. 2,560,892; sulfur dichloride and tetrachloride in U.S. Pat. No. 2,560,893; and silicon tetrafluoride in U.S. Pat. No. 2,560,894. The patents' stress on substantially anhydrous conditions is an important distinguishing feature.

The process of this application is a single stage method of preparing C-nitrosodiarylamines from their corresponding diarylamines. The success of the claimed invention rests on two separate and independent critical features. First, the described process requires the presence of water in a critical amount ranging from about 0.2 to about 18 gram per mole of diarylamine. Second, the success of the process also is dependent upon the addition of acid below the surface of the reaction mixture. The combination of these two features help define a novel single stage method of preparing C-nitrosodiarylamines from diarylamines in unusually high yield and with gratifyingly high purity.

SUMMARY OF THE INVENTION

One object of this invention is to prepare C-nitrosodiarylamines in a single stage process from diarylamines, thereby minimizing handling of and exposure to carcinogens. Another object is to effectuate said preparation in such manner as to improve the overall quality of the C-nitrosodiarylamine obtained while maintaining a high product yield. An embodiment comprises adding an alcoholic solution of a mineral acid below the surface of a stirred mixture of a diarylamine and alkali metal nitrite in an organic liquid containing from about 0.2 to about 18 grams water per mole diarylamine. In a more specific embodiment the alcohol is 1-butanol. In a still more specific embodiment the mineral acid is hydrogen chloride and the organic liquid is toluene. Other objects and embodiments will be apparent from the following description.

DESCRIPTION OF THE INVENTION

The invention described herein is a single stage process for the preparation of a C-nitrosodiarylamine from its diarylamine comprising adding from about 2 to about 6 molar proportions of a solution of a mineral acid in an anhydrous alcohol below the surface of a stirred mixture of 1 molar proportion of the diarylamine and an excess of a nitrite ion source in an organic liquid containing from about 0.2 to about 18 grams of water per mole of the diarylamine at a temperature less than about 60° C., and recovering the C-nitrosodiarylamine.

The invention as described has two features distinguishing it from the prior art methods. One distinguishing feature is that the water content of the reaction mixture is critical. If absolutely anhydrous conditions are maintained, the initial addition of acid causes precipitation of the acid salt of the diarylamine without release of nitrous acid and concomitant nitrosation. However, if too much water is present it has a deleterious effect on the rearrangement of the formed N-nitrosodiarylamine to the C-nitrosodiarylamine, instead effectuating, in part, denitrosation to the reactant diarylamine.

The second distinguishing feature of this invention is that addition of acid below the surface of the reaction mixture is necessary, especially as it affects the rearrangement of the intermediate N-nitrosodiarylamine to the product C-nitrosodiarylamine. It is thought essential that the local concentration of acid remain low during the rearrangement step, a requirement fulfilled only in part by effective mixing, but fulfilled in remaining part by introducing the acid below the surface of the stirred mixture.

The process of this invention is especially useful for diphenylamine and its corresponding C-nitroso product, p-nitrosodiphenylamine (PNODPA), but it is to be understood that it is applicable to other diarylamines as well. Examples of such amines, cited solely for illustrative purposes, include 2-methyldiphenylamine, 3-ethyldiphenylamine, 2-propyldiphenylamine, 2-butyldiphenylamine, 2-pentyldiphenylamine, 2-methoxydiphenylamine, 2-ethoxydiphenylamine, 2-propoxydiphenylamine, 2-butoxydiphenylamine, 2-pentoxydiphenylamine, 2-chlorodiphenylamine, 2-bromodiphenylamine, 2-iododiphenylamine, 2-fluorodiphenylamine, and similar diphenylamines substituted at the 3- or 4- position; 2,2'-dimethyldiphenylamine, 2-methoxy-2'-methyldiphenylamine, 4-cyclohexylaminodiphenylamine, phenyl beta-naphthylamine, di(alpha-naphthyl)amine, etc. Thus, one or both of the aromatic rings of the starting material may contain a substituent inert under the reaction conditions and which may be selected from alkyl of from 1 to about 5 carbon atoms, alkoxy of from 1 to about 5 carbon atoms, alkylamino of from 1 to about 5 carbon atoms, cycloalkylamino or other cycloalkyl containing substituents in which the cycloalkyl ring contains from 5 to 6 carbon atoms, aralkylamino and halogen.

The diarylamine used as the reactant in this invention is first dissolved in an organic liquid. An organic liquid is suitable for use in this invention if it is inert under the reaction conditions and can solubilize diarylamines. The organic liquids which are suitable include aromatic hydrocarbons containing from 6 to about 10 carbon atoms and chlorinated hydrocarbons. Illustrative of the aromatic hydrocarbons are benzene, toluene, xylene, ethylbenzene, mesitylene, cymene, and butylbenzene. Illustrative of chlorinated materials which may be used are chlorinated aromatics such as chlorobenzene, chlorinated alkyl aromatics such as chloromethylbenzene, chlorinated nitro aromatics such as chloronitrobenzene, chloromethylnitrobenzene, and chloroform. Toluene is often a preferred organic liquid for the combination of its boiling point and solubility properties.

The organic liquid contains water in an amount from 0.2 to about 18 grams per mole of diarylamine, and preferably from about 1 to about 3 grams per mole diarylamine. The function of this water is to solubilize a sufficient amount of nitrite ion source so that nitrous acid will be produced upon the addition of acid. It has been found that where water is present in a quantity less than the cited critical amount nitrosation does not proceed.

To this mixture is added an amount of a nitrite ion source slightly in excess of 1 molar proportion, based on the diarylamine. An excess from about 5 to about 20% is most generally employed. Sodium nitrite often is the most common source of nitrite ion, although other salts or alkyl nitrites such as potassium nitrite, sodium nitrite, lithium nitrite, butyl nitrite, propyl nitrite, ethyl nitrite, etc., may be used with equivalent results. The resulting suspension is mixed continuously, as by stirring, during subsequent reactions. Effective mixing is essential for the success of this invention, and mixing must be effective whatever the viscosity of the mixture.

A solution of an anhydrous mineral acid in an anhydrous alcohol is gradually added below the surface of this stirred mixture. It is essential that the local concentration of acid remain low during addition, a requirement which is fulfilled only in part by effective mixing, and in remaining part by introducing acid below the surface of the mixture. For the most effective practice of this invention, it is essential that the temperature be kept below about 60° C. throughout the process. It is preferred that the temperature be maintained below about 40° C. until preparation of the C-nitrosodiarylamine is complete, and maintenance of the temperature between about 20° C. and about 35° C. is particularly preferred.

Among the mineral acids which may be employed are the hydrogen halides, such as hydrogen chloride, hydrogen bromide, and hydrogen fluoride, with hydrogen chloride being the preferred acid.

The alcohols which may be used in this invention are saturated, aliphatic non-tertiary alcohols, either branched or straight chain, containing from about 4 to about 10 carbon atoms. Examples of suitable alcohols include the isomeric butanols, pentanols, hexanols, heptanols, octanols, nonanols, and decanols, although alcohols containing no more than about 6 carbon atoms are preferred. Among the preferred alcohols are included 1-butanol, 2,-butanol, 2-methyl-1-propanol, 1-pentanol, 2-pentanol, 3-pentanol, 2-methyl-1-butanol, 3-methyl-1-butanol, 1-hexanol, etc.

Alcoholic solutions containing from about 10 weight percent to about 40 weight percent of the mineral acid, or mixtures of mineral acids, often are the most convenient to use. In general, the higher the acid concentration the faster is the reaction and the greater is the chance of acid-catalyzed decomposition of the reaction product. Total amounts of added hydrogen halide, or other mineral acid, must be at least two molar proportions, based on the diphenylamine, and may range up to about 6 molar proportions. However, it has been found advantageous to use the minimum excess of hydrogen halide or other mineral acid feasible, and it is preferred to use from about 2.2 to about 3.5 molar proportions.

After about 1 molar proportion of acid has been added, the preparation of the N-nitrosodiarylamine is complete. Continued addition of the acid results in the rearrangement of the N-nitrosodiarylamine to the C-nitrosodiarylamine. The acid is added at such a rate that total addition times range from about 0.5 to about 5 hours, stirring and temperature control being maintained so that total reaction times are from about 1 to about 8 hours.

When the reaction is complete, the product is recovered by suitable means. Recovery generally begins by adjusting the pH with base until the final pH is from about 6 to about 7. In one embodiment, the base is an alkali metal bicarbonate, such as sodium bicarbonate, potassium bicarbonate, and lithium bicarbonate. In another embodiment, the pH adjustment is made by the addition of about 0.8 molar proportions, based on hydrogen chloride used in excess of the nitrite source, of an alkali metal hydroxide such as sodium hydroxide, potassium hydroxide, etc., followed by about 0.2 molar proportions of an alkali metal bicarbonate. The organic solvents then are removed by suitable means, and the C-nitrosodiarylamine is recovered, as by filtration. For example, when the alcohol is n-butanol and the other organic liquid is toluene, they may be effectively removed by steam distillation at reduced pressure such that the temperature of the mixture remains below about 60° C. The resulting aqueous suspension of PNODPA may thereafter be washed with toluene to remove tars, color bodies and other by-products, and the purified PNODPA may be collected by filtration.

The following examples are merely illustrative of this invention, which is not to be construed as limited thereto.

EXAMPLE I

To a 3 liter round bottom flask equipped with a stirrer thermometer, nitrogen gas blanket and addition funnel whose dip leg extended below the surface of the flask's contents was charged 169 g (1.0 mole) diphenylamine, 73 g (1.05 mole) sodium nitrite, 2 g (0.11 mole) water, and 200 g (2.17 mole) toluene. The addition funnel was charged with a mixture of 122 g (3.3 mole) anhydrous hydrogen chloride in 400 g anhydrous 1-butanol. The contents of the addition funnel were added below the surface of the reaction mixture over a period of 1 hour with vigorous stirring while the pot temperature was maintained between 20° and 30° C. using an external ice bath as required. The reaction mixture was stirred an additional 4 hours and then adjusted to a pH between 6 and 7 with a slurry of 194 g (2.3 mole) sodium bicarbonate in 300 g water while maintaining the pot temperature at 20° to 30° C. The aqueous layer was separated and discarded, and the organic layer was distilled at a pot temperature under 40° C. at 10 to 30 mm Hg for 3 hours. Water was added to the concentrate, the mass was stirred briefly, and solid was recovered by filtration and washed with additional water to remove remaining inorganic salts. The solid was air dried, weighed, and analyzed by high pressure liquid chromatography, which showed it to be PNODPA with a purity of 99% in 98% yield, and a melting point of 140° to 143° C.

EXAMPLE II

To a 3 liter round bottom flask equipped with a stirrer, thermometer, nitrogen gas blanket and addition funnel was charged 169 g (1.0 mole) diphenylamine, 73 g (1.05 mole) sodium nitrite, 2 g (0.11 mole) water, and 200 g (2.17 mole) toluene. The addition funnel was charged with a mixture of 122 g (3.3 mole) anhydrous hydrogen chloride in 400 g anhydrous 1-butanol. The contents of the addition funnel were added above the surface of the reaction mixture over a period of 1 hour with vigorous stirring while the pot temperature was maintained between 20° and 30° C. using an external ice bath when required. The reaction mixture was stirred an additional 4 hours and then adjusted to a pH between 6 and 7 with a slurry of 194 g (2.3 mole) sodium bicarbonate in 300 g water while maintaining the pot temperature at 20° to 30° C. The aqueous layer was separated and discarded, and the organic layer was distilled at a pot temperature under 40° C. at 10 to 30 mm Hg for 3 hours. Water was added to the concentrate, the mass was stirred briefly, and solid was recovered by filtration and washed with additional water to remove remaining inorganic salts. The solid was air dried, weighed, and analyzed by high pressure liquid chromatography, which showed it to be PNODPA with a purity of 89% in 88% yield, and a melting point of 136° to 140° C.

Thus, comparison with the results of Example I shows that addition below the surface increased the product purity from 89% to 99%, and increased product yield from 88% to 98%.

EXAMPLE III

This example was performed exactly the same as that of Example I except that water was not added. At the end of a 4 hour reaction time, following a 1 hour addition period, the reaction vessel contained a finely divided crystalline material which was removed by filtration. High pressure liquid chromatography and infrared analysis showed this solid to be diphenylamine hydrochloride which was recovered in a yield of 97 wt. %.

Thus, this example clearly demonstrates the necessity of having water present during the reaction for nitrosation to proceed.

What is claimed is:

1. A single stage process for the preparation of a C-nitrosodiarylamine from its diarylamine comprising adding from about 2 to about 6 molar proportions of a solution of a mineral acid in an anhydrous alcohol below the surface of a stirred mixture of 1 molar proportion of the diarylamine and an excess of a nitrite ion source in an organic liquid containing from about 0.2 to about 18 grams of water per mole of the diarylamine at a temperature less than about 60° C., and recovering said C-nitrosodiarylamine.

2. The process of claim 1 wherein the mineral acid is a hydrogen halide.

3. The process of claim 2 wherein the hydrogen halide is hydrogen chloride.

4. The process of claim 1 wherein said alcohol is a saturated, aliphatic, non-tertiary alcohol containing from 4 to about 10 carbon atoms.

5. The process of claim 4 wherein said alcohol contains from 4 to about 6 carbon atoms.

6. The process of claim 1 where said organic liquid comprises an aromatic compound selected from the group consisting of aromatic hydrocarbons containing from 6 to about 10 carbon atoms and chlorinated hydrocarbons.

7. The process of claim 6 where the aromatic hydrocarbon is selected from the group consisting of benzene, toluene, xylene, ethylbenzene, mesitylene, and cymene.

8. The process of claim 1 wherein the molar proportion of mineral acid is from about 2.2 to about 3.5.

9. The process of claim 1 wherein the organic liquid contains from about 1 to about 3 grams water per mole of the diarylamine.

10. The process of claim 1 wherein the reaction temperature is maintained below about 40° C.

11. The process of claim 10 wherein the reaction temperature is maintained from about 20° C. to about 35° C.

* * * * *